(12) United States Patent
Fuerst et al.

(10) Patent No.: US 11,896,315 B2
(45) Date of Patent: Feb. 13, 2024

(54) VIRTUAL REALITY SYSTEM WITH CUSTOMIZABLE OPERATION ROOM

(71) Applicant: Verb Surgical Inc., Santa Clara, CA (US)

(72) Inventors: Bernhard Fuerst, Sunnyvale, CA (US); Eric Johnson, Pacific Grove, CA (US); Pablo Garcia Kilroy, Menlo Park, CA (US)

(73) Assignee: VERB SURGICAL INC., Santa Clara, CA (US)

( * ) Notice: Subject to any disclaimer, the term of this patent is extended or adjusted under 35 U.S.C. 154(b) by 0 days.

(21) Appl. No.: 17/839,153

(22) Filed: Jun. 13, 2022

(65) Prior Publication Data

US 2022/0296307 A1    Sep. 22, 2022

Related U.S. Application Data

(63) Continuation of application No. 16/667,237, filed on Oct. 29, 2019, now Pat. No. 11,382,696, and a continuation of application No. 16/667,241, filed on Oct. 29, 2019, now Pat. No. 11,389,246.

(51) Int. Cl.
| | |
|---|---|
| *A61B 34/10* | (2016.01) |
| *G06T 19/20* | (2011.01) |
| *G16H 20/40* | (2018.01) |
| *G16H 40/63* | (2018.01) |

(Continued)

(52) U.S. Cl.
CPC .............. *A61B 34/10* (2016.02); *G06T 15/20* (2013.01); *G06T 19/20* (2013.01); *G16H 20/40* (2018.01); *G16H 40/63* (2018.01); *A61B 34/30* (2016.02); *A61B 2034/104* (2016.02); *A61B 2034/105* (2016.02); *A61B 2034/107* (2016.02);

(Continued)

(58) Field of Classification Search
None
See application file for complete search history.

(56) References Cited

U.S. PATENT DOCUMENTS

| | | | |
|---|---|---|---|
| 10,712,923 B1 * | 7/2020 | Pathmanathan | .... G06F 3/04815 |
| 11,314,846 B1 * | 4/2022 | Colin | ..................... G16H 40/40 |
| 2010/0211897 A1 | 8/2010 | Cohen et al. | |

(Continued)

FOREIGN PATENT DOCUMENTS

| | | |
|---|---|---|
| WO | 2016149794 | 9/2016 |
| WO | 2019006202 | 1/2019 |
| WO | 2019148286 | 8/2019 |

OTHER PUBLICATIONS

Non-Final Office Action for U.S. Appl. No. 16/840,144 dated Aug. 4, 2022, 17 pages.

(Continued)

*Primary Examiner* — Kyle Zhai
(74) *Attorney, Agent, or Firm* — Aikin & Gallant, LLP

(57) ABSTRACT

A virtual operating room (OR) is generated that includes virtual surgical equipment based on existing OR models and existing equipment models. Sensor feedback is received that defines a physical OR having physical equipment, the physical equipment including a surgical robotic system within the physical OR. The virtual OR and the virtual surgical equipment is updated based on the sensor feedback. A layout of the virtual surgical equipment is optimized in the virtual OR. The virtual OR and the virtual surgical equipment are rendered on a display.

18 Claims, 6 Drawing Sheets

(51) Int. Cl.
*G06T 15/20* (2011.01)
*A61B 34/30* (2016.01)

(52) U.S. Cl.
CPC .. *G06T 2210/41* (2013.01); *G06T 2219/2016* (2013.01); *G06T 2219/2021* (2013.01)

(56) References Cited

U.S. PATENT DOCUMENTS

| | | |
|---|---|---|
| 2011/0061011 A1 | 3/2011 | Hoguet |
| 2013/0245375 A1 | 9/2013 | DiMaio et al. |
| 2014/0018960 A1 | 1/2014 | Itkowitz |
| 2016/0314710 A1 | 10/2016 | Jarc et al. |
| 2017/0049517 A1 | 2/2017 | Felder et al. |
| 2017/0319282 A1 | 11/2017 | Jarc et al. |
| 2018/0098813 A1 | 4/2018 | Nesichi et al. |
| 2018/0116724 A1 | 5/2018 | Gmeiner et al. |
| 2018/0280099 A1 | 10/2018 | Cone et al. |
| 2018/0324539 A1 | 11/2018 | Lovitt |
| 2018/0338806 A1 | 11/2018 | Grubbs |
| 2018/0350145 A1* | 12/2018 | Byl ............... G06T 19/006 |
| 2019/0005848 A1 | 1/2019 | Garcia Kilroy et al. |
| 2019/0279524 A1 | 9/2019 | Stoyanov et al. |
| 2019/0307510 A1 | 10/2019 | Rotenberg et al. |
| 2019/0318640 A1 | 10/2019 | Goel et al. |
| 2019/0325574 A1 | 10/2019 | Jin et al. |
| 2020/0038124 A1 | 2/2020 | Lin et al. |
| 2020/0074402 A1 | 3/2020 | Adato et al. |

OTHER PUBLICATIONS

International Preliminary Report on Patentability for International Application No. PCT/US2020/031367 dated Oct. 13, 2022, 6 pages.
International Search Report and Written Opinion for International Application No. PCT/US2019/064713 dated Jul. 21, 2020, 9 pages.
Non-Final Office Action for U.S. Appl. No. 16/667,237 dated Mar. 31, 2021, 17 pages.
Non-Final Office Action for U.S. Appl. No. 16/870,586 dated Mar. 31, 2021, 21 pages.
Final Office Action for U.S. Appl. No. 16/667,237 dated Aug. 26, 2021, 15 pages.
Non-Final Office Action for U.S. Appl. No. 16/667,237 dated Nov. 22, 2021, 14 pages.
Almusawi, A.J.R., et al., "Simulation in virtual reality: Robotic training and surgical applications," Scientia Iranica B (2019), 26(6), pp. 3369-3374.
International Preliminary Report on Patentability for International Application No. PCT/US2019/064713 dated May 12, 2022, 6 pages.
Office Action for U.S. Appl. No. 16/667,237 dated Mar. 16, 2022, 5 pages.
Non-Final Office Action for U.S. Appl. No. 16/667,241 dated Apr. 27, 2021, 17 pages.
Final Office Action for U.S. Appl. No. 16/667,241 dated Aug. 26, 2021, 13 pages.
Chen, Xiaowu, et al., "Image2Scene: Transforming Style of 3D Room," ACM, 2015, 4 pages.
Non-Final Office Action for U.S. Appl. No. 16/667,241 dated Nov. 24, 2021, 15 pages.
Valentini, Pier Paolo, "Interactive cable harnessing in augmented reality," Int. J. Interact. Des. Manuf. (2011) 5:45-53.
Office Action for U.S. Appl. No. 16/667,241 dated Mar. 16, 2022, 5 pages.

* cited by examiner

VIRTUAL REALITY SYSTEM WITH CUSTOMIZABLE OPERATION ROOM

CROSS-REFERENCE TO RELATED APPLICATIONS

The application is a continuation of pending U.S. application Ser. No. 16/667,241 filed Oct. 29, 2019, and is a continuation of pending U.S. application Ser. No. 16/667,237 filed Oct. 29, 2019.

TECHNICAL FIELD

This invention relates generally to surgical robotic systems, and more specifically to systems and methods to plan for a surgical robotic procedure.

BACKGROUND

Minimally-invasive surgery (MIS), such as laparoscopic surgery, involves techniques intended to reduce tissue damage during a surgical procedure. For example, laparoscopic procedures typically involve creating a number of small incisions in the patient (e.g., in the abdomen), and introducing one or more tools and at least one camera through the incisions into the patient. The surgical procedures can then be performed by using the introduced surgical tools, with the visualization aid provided by the camera.

Generally, MIS provides multiple benefits, such as reduced patient scarring, less patient pain, shorter patient recovery periods, and lower medical treatment costs associated with patient recovery. MIS can be performed with surgical robotic systems that include one or more robotic arms for manipulating surgical tools based on commands from a remote operator. A robotic arm may, for example, support at its distal end various devices such as surgical end effectors, imaging devices, cannulas for providing access to the patient's body cavity and organs, etc. Thus, a surgical robotic arm can assist in performing surgery.

Control of such robotic systems may require control inputs from a user (e.g., surgeon or other operator) via one or more user interface devices that translate manipulations or commands from the user into control of the robotic system. For example, in response to user commands, a tool driver having one or more motors may actuate one or more degrees of freedom of a surgical tool when the surgical tool is positioned at the surgical site in the patient.

SUMMARY

It may be desirable to plan a surgical robotic workflow that describes an arrangement of surgical robotic arms in advance of a procedure. By determining the arrangement prior to surgery with the processes discussed herein, one can improve the repeatability of success of the operation and beneficially determine which physical environments (e.g., operating rooms in a health facility) will be adequate for a particular surgical robotic environment. The arrangement (e.g., location and orientation) of the surgical robotic system (e.g., the surgical robotic arms, the surgical robotic platform, the user console, the control tower, and other surgical robotic equipment) can be planned and optimized based on the processes discussed herein.

In some embodiments, a system and process for planning surgical robotic workflow with a surgical robotic system is described. A virtual surgical environment is generated, having one or more virtual surgical robotic arms and a virtual patient. A workspace is determined in the virtual patient. A position of each of one or more virtual tools is determined based on the workspace. A position of each of the one or more virtual surgical robotic arms is determined based on the positions of the virtual tools, to maintain a reach of the virtual tool in the workspace.

In some embodiments, determining surgical robotic workflow and layout for a surgical robotic procedure can be incrementally improved. A workflow and a layout of virtual surgical equipment is determined. The layout is used as a reference to arrange a physical layout. The physical layout can then be used as a reference to re-arrange the virtual surgical robotic equipment. Thus, a two-way improvement process can help setup of a surgical robotic system in a physical environment. For example, a virtual operating room (OR) and virtual surgical equipment can be generated based on existing OR models and existing equipment models. Sensor feedback is received defining a physical OR having physical equipment including a surgical robotic system within the physical OR. The virtual OR and the virtual surgical equipment is updated based on the sensor feedback. The layout of the virtual surgical equipment is optimized in the virtual OR. The optimized layout of the virtual surgical equipment can be rendered on a display, which can be used as reference to rearrange the physical surgical equipment in the physical OR. The process can be repeated.

DETAILED DESCRIPTION

Examples of various aspects and variations of the invention are described herein and illustrated in the accompanying drawings. The following description is not intended to limit the invention to these embodiments, but rather to enable a person skilled in the art to make and use this invention.

The following description and drawings are illustrative of the disclosure and are not to be construed as limiting the disclosure. Numerous specific details are described to provide a thorough understanding of various embodiments of the present disclosure. However, in certain instances, well-known or conventional details are not described in order to provide a concise discussion of embodiments of the present disclosures.

Reference in the specification to "one embodiment" or "an embodiment" means that a particular feature, structure, or characteristic described in conjunction with the embodiment can be included in at least one embodiment of the disclosure. The appearances of the phrase "in one embodiment" in various places in the specification do not necessarily all refer to the same embodiment.

Figure 1:
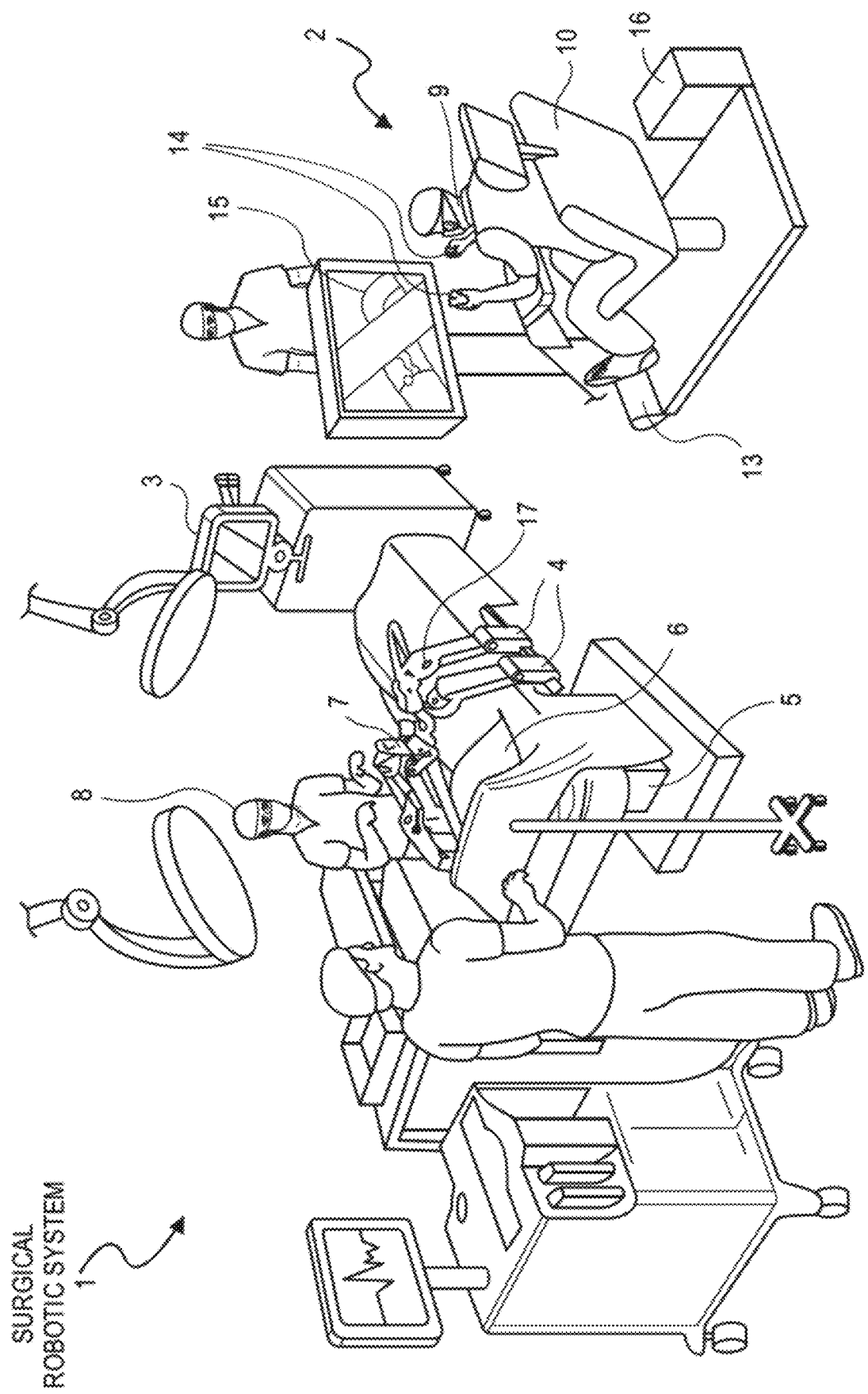
FIG. 1 illustrates a surgical robotic system, according to one embodiment.

Referring to FIG. 1, this is a pictorial view of an example surgical robotic system 1 in an operating arena. The robotic system 1 includes a user console 2, a control tower 3, and one or more surgical robotic arms 4 at a surgical robotic platform 5, e.g., a table, a bed, etc. The system 1 can incorporate any number of devices, tools, or accessories used to perform surgery on a patient 6. For example, the system 1 may include one or more surgical tools 7 used to perform surgery. A surgical tool 7 may be an end effector that is attached to a distal end of a surgical arm 4, for executing a surgical procedure.

Each surgical tool 7 may be manipulated manually, robotically, or both, during the surgery. For example, the surgical tool 7 may be a tool used to enter, view, or manipulate an internal anatomy of the patient 6. In an embodiment, the surgical tool 7 is a grasper that can grasp tissue of the patient. The surgical tool 7 may be controlled manually, by a bedside operator 8; or it may be controlled robotically, via actuated movement of the surgical robotic arm 4 to which it is attached. The robotic arms 4 are shown as a table-mounted system, but in other configurations the arms 4 may be mounted in a cart, ceiling or sidewall, or in another suitable structural support.

Generally, a remote operator 9, such as a surgeon or other operator, may use the user console 2 to remotely manipulate the arms 4 and/or the attached surgical tools 7, e.g., teleoperation. The user console 2 may be located in the same operating room as the rest of the system 1, as shown in FIG. 1. In other environments however, the user console 2 may be located in an adjacent or nearby room, or it may be at a remote location, e.g., in a different building, city, or country. The user console 2 may comprise a seat 10, foot-operated controls 13, one or more handheld user input devices, UID 14, and at least one user display 15 that is configured to display, for example, a view of the surgical site inside the patient 6. In the example user console 2, the remote operator 9 is sitting in the seat 10 and viewing the user display 15 while manipulating a foot-operated control 13 and a handheld UID 14 in order to remotely control the arms 4 and the surgical tools 7 (that are mounted on the distal ends of the arms 4.)

In some variations, the bedside operator 8 may also operate the system 1 in an "over the bed" mode, in which the beside operator 8 (user) is now at a side of the patient 6 and is simultaneously manipulating a robotically-driven tool (end effector as attached to the arm 4), e.g., with a handheld UID 14 held in one hand, and a manual laparoscopic tool. For example, the bedside operator's left hand may be manipulating the handheld UID to control a robotic component, while the bedside operator's right hand may be manipulating a manual laparoscopic tool. Thus, in these variations, the bedside operator 8 may perform both robotic-assisted minimally invasive surgery and manual laparoscopic surgery on the patient 6.

During an example procedure (surgery), the patient 6 is prepped and draped in a sterile fashion to achieve anesthesia. Initial access to the surgical site may be performed manually while the arms of the robotic system 1 are in a stowed configuration or withdrawn configuration (to facilitate access to the surgical site.) Once access is completed, initial positioning or preparation of the robotic system 1 including its arms 4 may be performed. Next, the surgery proceeds with the remote operator 9 at the user console 2 utilizing the foot-operated controls 13 and the UIDs 14 to manipulate the various end effectors and perhaps an imaging system, to perform the surgery. Manual assistance may also be provided at the procedure bed or table, by sterile-gowned bedside personnel, e.g., the bedside operator 8 who may perform tasks such as retracting tissues, performing manual repositioning, and tool exchange upon one or more of the robotic arms 4. Non-sterile personnel may also be present to assist the remote operator 9 at the user console 2. When the procedure or surgery is completed, the system 1 and the user console 2 may be configured or set in a state to facilitate post-operative procedures such as cleaning or sterilization and healthcare record entry or printout via the user console 2.

In one embodiment, the remote operator 9 holds and moves the UID 14 to provide an input command to move a robot arm actuator 17 in the robotic system 1. The UID 14 may be communicatively coupled to the rest of the robotic system 1, e.g., via a console computer system 16. The UID 14 can generate spatial state signals corresponding to movement of the UID 14, e.g. position and orientation of the handheld housing of the UID, and the spatial state signals may be input signals to control a motion of the robot arm actuator 17. The robotic system 1 may use control signals derived from the spatial state signals, to control proportional motion of the actuator 17. In one embodiment, a console processor of the console computer system 16 receives the spatial state signals and generates the corresponding control signals. Based on these control signals, which control how the actuator 17 is energized to move a segment or link of the arm 4, the movement of a corresponding surgical tool that is attached to the arm may mimic the movement of the UID 14. Similarly, interaction between the remote operator 9 and the UID 14 can generate for example a grip control signal that causes a jaw of a grasper of the surgical tool 7 to close and grip the tissue of patient 6.

The surgical robotic system 1 may include several UIDs 14, where respective control signals are generated for each UID that control the actuators and the surgical tool (end effector) of a respective arm 4. For example, the remote operator 9 may move a first UID 14 to control the motion of an actuator 17 that is in a left robotic arm, where the actuator responds by moving linkages, gears, etc., in that arm 4. Similarly, movement of a second UID 14 by the remote operator 9 controls the motion of another actuator 17, which in turn moves other linkages, gears, etc., of the robotic system 1. The robotic system 1 may include a right arm 4 that is secured to the bed or table to the right side of the patient, and a left arm 4 that is at the left side of the patient. An actuator 17 may include one or more motors that are controlled so that they drive the rotation of a joint of the arm 4, to for example change, relative to the patient, an orientation of an endoscope or a grasper of the surgical tool 7 that is attached to that arm. Motion of several actuators 17 in the same arm 4 can be controlled by the spatial state signals generated from a particular UID 14. The UIDs 14 can also control motion of respective surgical tool graspers. For example, each UID 14 can generate a respective grip signal to control motion of an actuator, e.g., a linear actuator, that opens or closes jaws of the grasper at a distal end of surgical tool 7 to grip tissue within patient 6.

In some embodiments, the communication between the platform 5 and the user console 2 may be through a control tower 3, which may translate user commands that are received from the user console 2 (and more particularly from the console computer system 16) into robotic control commands that transmitted to the arms 4 on the robotic platform 5. The control tower 3 may also transmit status and feedback from the platform 5 back to the user console 2. The communication connections between the robotic platform 5, the user console 2, and the control tower 3 may be via wired and/or wireless links, using any suitable ones of a variety of data communication protocols. Any wired connections may be optionally built into the floor and/or walls or ceiling of the operating room. The robotic system 1 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

A surgical robotic arm can have movable, jointed, and/or motorized members with multiple degrees of freedom that can hold various tools or appendages at distal ends. Example systems include the da Vinci® Surgical System which can be used for minimally invasive surgery (e.g., urologic surgical procedures, general laparoscopic surgical procedures, gynecologic laparoscopic surgical procedures, general non-cardiovascular thoracoscopic surgical procedures and thoracoscopically assisted cardiotomy procedures). A "virtual surgical robotic arm" can be a computer generated representation of a robotic arm rendered over the captured video of a user setup. The virtual surgical robotic arm can be a complex 3D model of the real robotic arm. Alternatively or additionally a virtual surgical robotic arm can include visual aids such as arrows, tool tips, or other representation relating to providing pose information about a robotic arm such as a geometrically simplified version of the real robotic arm.

System for Generating and Optimizing a Workflow Setup

Figure 2:
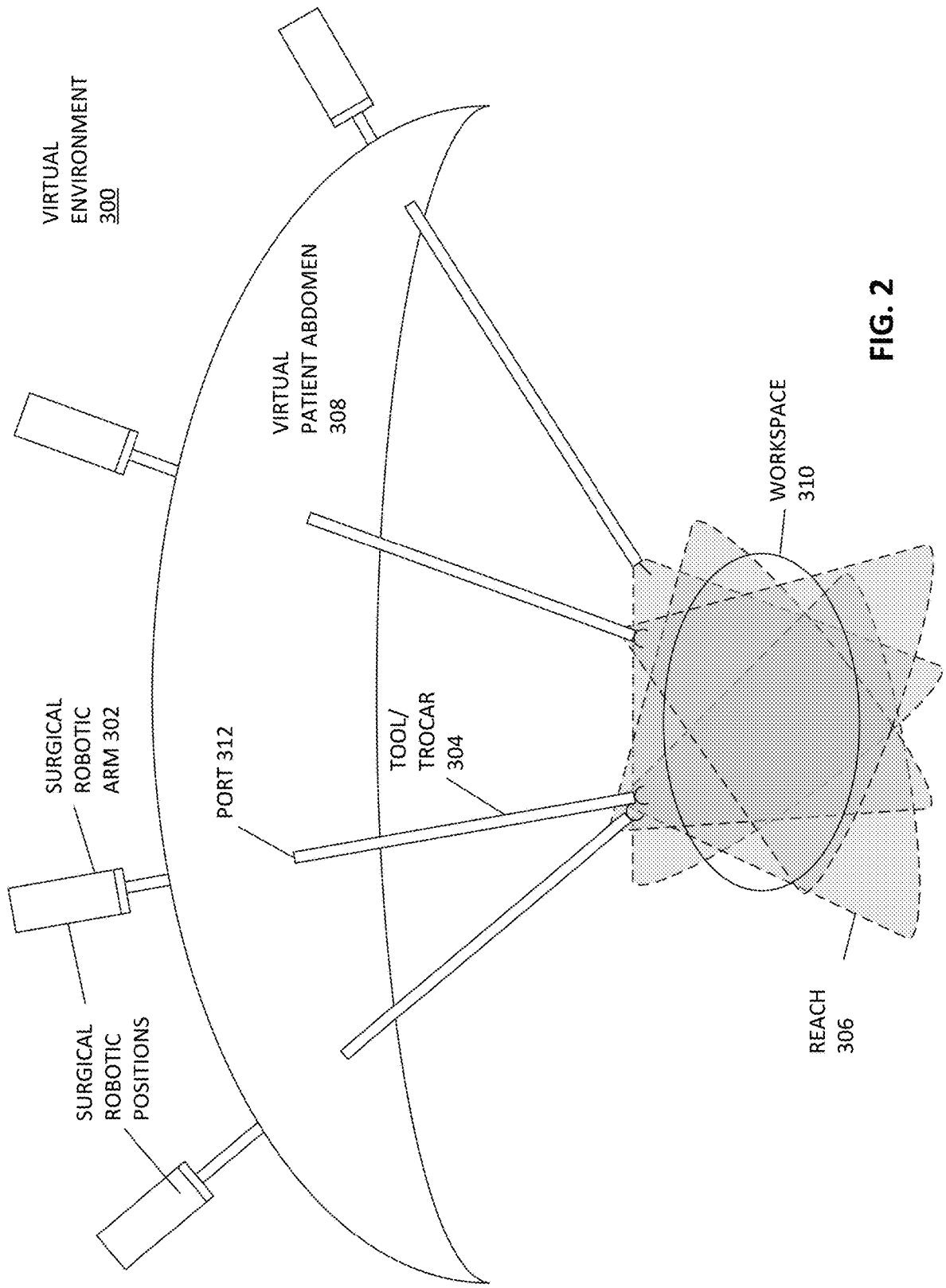
FIG. 2 illustrates a workflow for a surgical robotic system, according to one embodiment.

A workflow for a surgical robotic system describes preparation of surgical equipment so that a procedure can be performed in an area of a patient known as a workspace. Workflow optimization can include determining workspace, tool placement, port locations, and setup of surgical robotic arms, to prepare for a surgical procedure. Referring to FIG. 2, workflow can be optimized in a virtual environment 300 to reduce risk of collision and maximize reachability of tools in a workspace. It should be understood that 'virtual' as used herein can describe a computer generated representation of an object (e.g., surgical equipment, rooms, and/or people) in two dimensional or three dimensional space. Virtual equipment can be generated that is representative of corresponding real-life counterparts, defining a size and a shape. For example, a virtual surgical robotic arm can be representative of a real surgical robotic arm, a virtual subject can be representative of a real-life patient, and a virtual operating room can be representative of a real operating room. A computer model of an object is a grouping of data that describes attributes of a physical object such as, but not limited to, surgical equipment and patients. Virtual objects can be generated based on the computer models.

A workspace 310 in a virtual patient can be defined, for example, based on procedure type, patient anatomy, a patient size, etc. A position of a tool 304 can be determined based on the workspace and/or a reach 306 of a surgical tool within the workspace. A tool can include a trocar and/or additional surgical tools (for example, stapler, grasper, scissor, and camera). A port 312 can be determined based on where the trocar passes through the virtual patient's abdomen 308. A position of a virtual surgical robotic arm 302 can be determined based on the port location, the trocar position, and/or the workspace.

An initial setup of each robotic arm can be determined, for example, whether each robotic arm is in a stowed position, draped or docked. Proper setup of each robotic arm prior to a procedure places arms and attached tools in position to enter and operate upon the workspace. Improper setup can cause delays during a procedure and increase the risk of mistake and/or harm to a patient. The mechanical movements that each arm is capable of is considered in determining arm setup, to enable reach of surgical tools in the workspace.

A procedure may require that one or more of the surgical robotic arms be able to reach the workspace 310 at various stages of the procedure. Optimizing a workflow can include determining the trocar placements so that reach 306 of tools through the trocar are sufficient in the workspace. In some cases, workflow optimization can determine positions of the trocars, ports and surgical robotic arms so that reach of the two or more robots and corresponding tools overlap in the workspace. Optimization, as used herein, can refer to software and hardware supported algorithms that arrange virtual surgical equipment (e.g., workflow and/or layout) based on one or more criteria and inputs described herein such as, but not limited to, location of a workspace, reach and movements in a workspace, convenience, and risk of collisions. Optimization does not require that an optimal arrangement is reached. Rather, the arrangement of the virtual equipment, and/or the virtual OR is improved, sometimes incrementally, based on the criteria.

Figure 3:
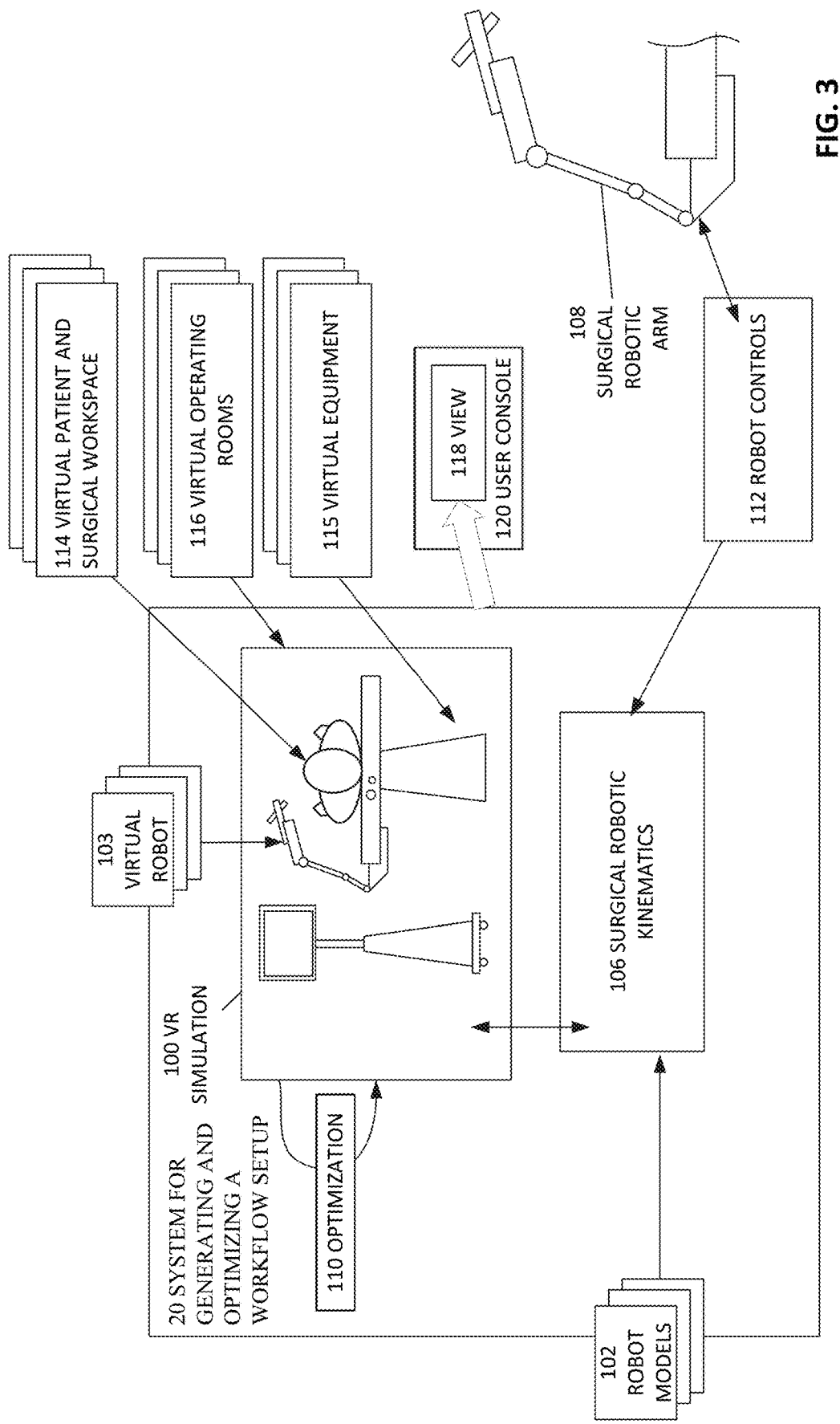
FIG. 3 shows a system for generating and optimizing a workflow setup, according to one embodiment.

Referring to FIG. 3, a system 20 for generating and optimizing a workflow setup is shown. The system can generate a virtual reality (VR) simulation 100 of an operating room and surgical equipment, also described herein as a virtual surgical environment. Such a simulation can include a virtual patient 114, and virtual surgical equipment (including one or more virtual robotic arms 103) representative of the surgical robotic system described in FIG. 1. The virtual surgical robotic equipment and the virtual patient can be arranged in a virtual operating room, to help plan for a surgical robotic procedure (e.g., laparoscopic surgery).

A surgical robotic kinematics processor 106 can generate kinematics parameters that define movement restraints and movement abilities of a physical surgical robotic arm. For example, each robotic arm can have various interconnected members, each of which can move rotate or travel in one or more defined directions, planes, or axis. Movements can be bound, for example, by angles or distances of travel. Thus, the kinetic parameters can define how a surgical robotic arm and surgical robotic tool can or cannot move, which in turn, determines a reach and movement capabilities of a tool in a workspace.

In one embodiment, the kinetic parameters are defined in robot models 102 (e.g., computer aided drawing (CAD) models or unified robot description format (URDF) models). The kinematics processor can extract these parameters from the models to be used in determining the setup of the virtual surgical robotic arm or the virtual tool in the VR simulation.

Alternatively or additionally, the kinematics processor can generate the kinematic parameters based on robot control data (e.g. motor/actuator commands and feedback, servo commands, position data, and speed data) generated by robot controls 112. The robot control data can be generated during an actual surgical procedure using a real surgical robotic arm and/or surgical tool 108, or a simulated surgical procedure (e.g., a test run), also using a real surgical robotic arm and/or tool.

In one embodiment, the kinematics parameters are generated based on the robot models and based on the robot control data. The kinematics parameters can be extracted from the robot models 102, and then modified based on real world data received from the robot controls 112.

In one embodiment, the kinematics parameters can also include dynamic information such as mass, inertia, gravity, force, and torque of the robotic arm. The dynamic information can be generated based on the inputs from the real robot controls 112 and/or the robot models. These inputs can include control feedback, motor control data and sensor data of a real surgical robotic arm 108.

Thus, the kinematics modeling can benefit from physical feedback as well as computer-generated restraints to generate a kinematics model that resembles real-life kinematics of the robotic arm. Beneficially, by using real data from a physical robotic arm, the kinematics parameters can provide accuracy in determining the arrangement of the virtual robotic arms relative to the workspace and virtual patient. Accordingly, based on the movement constraints and capabilities of a physical surgical robotic arm and/or tool, the virtual robotic arm can be arranged relative to the virtual patient in the VR simulation to enable proper movements within the workspace of the virtual patient, as required by a particular surgical procedure.

In one embodiment, an optimization procedure 110 is performed to arrange the virtual objects (e.g., the patient, the robotic arm and tool, the platform, the user console, the control tower, and other surgical equipment) based on one or more inputs and changes to inputs. For example, inputs can workspace, patient geometry, operating room, procedure type, platform height, etc. Changes to inputs can include a modification to a virtual patient, a change to a procedure, a change to the operating room, a change to platform height, and/or any change that would modify a location or size of a workspace in a virtual patient. In some cases, a user interface can allow a user to manually move a virtual object in a VR simulation while wearing a headset having a head-up display. The user can be immersed in the VR simulation. Based on one or more inputs, the optimization procedure can rearrange the virtual objects and re-optimize.

In one embodiment, the optimization procedure 110 includes operations for planning surgical robotic workflow with a surgical robotic system. The operations include: generating a virtual surgical environment, the virtual surgical environment including a virtual surgical robotic arm and a virtual patient. A workspace in the virtual patient can be determined (e.g., based on a procedure type and the virtual patient). A position of a virtual tool (e.g., a trocar and other tools introduced through the trocar) can be determined based on the workspace. A position of the virtual surgical robotic arm, on which the virtual tool is attached, is determined based on the position of the virtual tool, to maintain a reach of the virtual tool in the workspace.

In one embodiment, the kinematics parameters can be generated that define movement constraints of a surgical robotic arm to be used in the procedure type. For example, the kinematics parameters can define a direction that a member of the robot moves, a maximum or minimum distance or angle that each member can travel, the mass of each member, the stiffness of each member, and/or speed and force in which members move. Thus, the arranging of the virtual surgical robotic arm or the virtual tool can further be based on the kinematics parameters of the virtual robotic arm so that the virtual surgical robotic arm can perform the surgical procedures type within the surgical workspace, with reference to the kinematics parameters.

In one embodiment, the VR simulation can include virtual equipment 115 such as a surgical robotic platform, a control tower, a user console, scanning equipment (e.g., mobile X-ray machine (C-arm) or ultrasound imaging machine), stands, stools, trays, and other equipment that would be arranged in a surgical operating room. The virtual equipment can be generated based on computer models that define parameters such as shape and size of the various equipment.

In one embodiment, an operating room can be generated in the VR simulation. The other virtual objects can be arranged in the virtual operating room to plan a surgical layout and workflow in a particular operating room. The virtual operating room 116 can be based on a physical operating room to plan for a procedure in the physical operating room. The virtual operating room can be rendered from one of many operating room models, stored in electronic memory. A virtual operating room can be a) generated from a three-dimensional scanning of a physical room, b) generated based on a model selected from a database containing a one or more operating room models, or c) generated based on room parameters (e.g., length and width of walls, ceilings, floors, doorways, windows, and more).

One or more virtual patients 114 can be generated by scanning a real life patient. Virtual patients 114 can be adjusted or improved based on data captured during a procedure. In one embodiment, virtual patients 114 can have modeled internal organs. A workspace can be determined based on data that identifies locations and geometry of internal organs.

Virtual patients and workspaces can be determined in a virtual environment, using the patient models. Surgical workspaces can be defined in virtual patients based on the type of surgical procedure. For example, a particular surgical procedure may define the surgical workspace of a virtual patient as an area below the belly button, intestines, liver, gallbladder, etc. Thus, understanding anatomy of patients (e.g., location of organs) can be of high importance in determining a setup of the robotic arms and tool, and port positions. Through scanning real life patients, and then using real surgical data, the accuracy of the virtual patients and workspace locations in the virtual patients can be improved, thereby improving the planning of the surgical workflow. Port positions can be accurately determined, and reach of tools within a workspace can be improved.

A geometry and anatomy of a virtual patient can be determined based on sensor information or surgical robotic movement data, captured from one or more surgical procedures. The surgical procedures can be real surgical procedures or simulated procedures with real patients or dummies. Generating or modifying the virtual patient can include estimating internal volume and/or anatomy of the virtual patient based on sensors such as a) camera images taken internal of a patient, and/or b) surgical robotic tool motions, captured during the one or more surgical procedures.

Additionally or alternatively, generating or modifying the virtual patient can include reconstructing internal volume of a patient model based on endoscope data captured during one or more surgical procedures. The patient model can be generated based on a 3D scanning of a real patient. Additionally or alternatively, the patient model can be generated based on the sensor data (e.g., cameras and other medical imaging technology). In the case where 3D scanning is performed, the patient model can be modified based on the sensor information (e.g., captured by a surgical tool) or the surgical robotic movement data. Beneficially, reconstruction of the patient model can fill in for missing parts or deficient definitions of the patient model, for example, if the 3D scanning did not provide enough information.

Where a patient model is determined to be deficient, areas of the patient model can be reconstructed to supplement the missing or deficient patient model information. For example, if the location of the liver of a patient model is unclear based on the 3D scanning, the sensor information or surgical robotic movement data can be used to reconstruct that area of the patient model. The information and data can be captured and stored in a real surgical log during a procedure. For example, during a real surgical procedure, data can be generated regarding the internal anatomy (e.g., organ sizes and wall thicknesses, and more) and internal volume of a patient based on remote center of motion (RCM) mechanisms, camera generated images, other imagery, and/or other surgical robotic tool motions.

In one embodiment, the VR simulation 100 can be communicated or output through a display, for example, on a user console 120. A view generator can generate one or more views 118 of the VR simulation, for example, a stadium view or first person view. Such view can be used by a user to further generate inputs to the optimizer 20. For example, a user can use the user console 120 to modify or replace the virtual patient, a workspace, virtual surgical equipment, and/or a virtual operating room. The VR simulation can be optimized at block 110 based on the adjustments made by the user. The view of the simulation can then be re-generated for the user, thus providing adjustments and optimization of the workflow based on user generated inputs. In this manner, the user can tailor the workflow and layout optimization to suit a particular patient and procedure type. This can streamline setup of robotic arms for different patients, different procedures, and help selection of operating rooms to facilitate such procedures.

In some embodiments, the VR simulation can be generated as a 2D model. For example, the VR simulation can be generated as a plan view, which can beneficially provide an instant understanding of the location of each object in an operating room and the spacing between the models.

Figure 4:
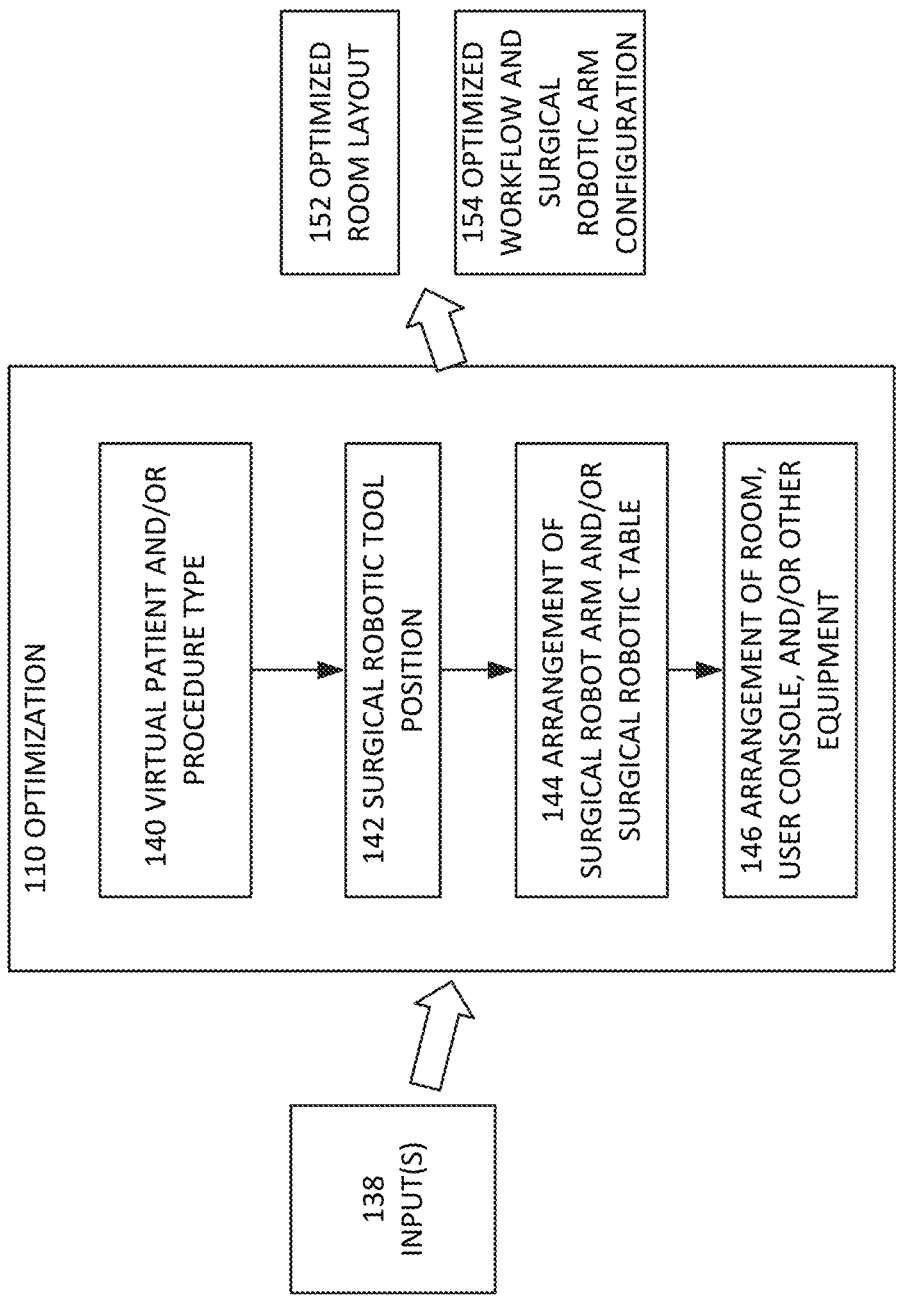
FIG. 4 shows a process for optimizing a virtual surgical environment, according to one embodiment.

In one embodiment, as shown in FIG. 4, an optimization process 110 can optimize a room layout 152 and surgical robotic arm configuration 154, based on one or more inputs 138. The inputs can include changes to one or more of the following factors: the procedure type, the surgical workspace, the virtual patient, the tool position, and kinematics parameters.

For example, as mentioned in regard to FIG. 2, an initial input can include a location of a workspace 310 within a virtual subject 308. A position of a trocar 304 can be determined based on the workspace and a reach 306 of a tool (e.g., scissor, stapler, grasper or needle) within the workspace. A port location 312 can be determined based on the position of the trocar and/or the workspace. A position of the surgical robotic arm can be determined based on the location of the port, the workspace, and/or trocar position.

Changes in a patient model, surgical tool position, robot kinematics, or surgical workspace can initiate an adjustment to the setup of the robotic arm. For example, if a size of a virtual patient changes, this can cause a change in a location of the workspace. The trocar position is adjusted to maximize the reach of a tool within the changed location of the workspace. The port location and position of the surgical robotic arm can be adjusted accordingly. It should be understood that 'setup', 'configuration', and 'arrangement' as discussed with relation to the robotic arm and tool can describe the manner in which members of the robotic arm and/or tool is positioned, either absolutely or relative to one another. Thus, the 'setup' or 'configuration' of the robotic arm can describe a particular pose of the robotic arm and a position of the tool which is attached to the robotic arm.

In one embodiment, changes in the location or orientation of virtual surgical equipment (e.g., user console, scanning equipment, control tower) or staff personnel models can initiate a rearrangement of the virtual surgical equipment. Similarly, changes to a procedure type can initiate changes in the surgical workspace in a virtual patient which, in turn, can cause a change in default tool positions (e.g., a default trocar position), port locations, and surgical robotic arm positions. Similarly, changes in a virtual patient (for example, taller or heavier build) can initiate a change in the surgical workspace of the virtual patient, which can cause a ripple effect in tool position, port location, and surgical robotic arm configuration. Similarly, a change in platform position (e.g., height, angle or slope of table) can similarly initiate changes in the tool position, port location, and robotic arm configuration, given that the virtual patient is laid upon the platform during the virtual procedure.

Referring to FIG. 4, the optimization process 110 can generate an optimized a room layout 152 and surgical robotic arm configuration 154 supports tool positions to have adequate reach within a defined workspace. The optimization process can have a hierarchy of operations based on a ranked order of importance. Blocks 140, 142, 144, and 146 can be performed sequentially in the order shown.

For example, at block 140, a virtual patient and/or surgical robotic procedure type can have a highest rank of importance. A workspace within a patient can be determined based on procedure type and/or the virtual patient can determine the workspace within the patient (e.g., some area below the virtual patient's abdomen). The workspace area can define a location, size, and/or shape in a virtual patient where the procedure is to occur.

Next, in block 142, a surgical robotic tool position (e.g., a default tool position) can be defined and arranged. The position of the surgical tool can be based on the surgical workspace. For example, as shown in FIG. 2, a position (e.g., location and orientation) of one or more tools 304 can be determined based on the reach 306 of each tool and workspace location 310. One or more port locations 312 can be determined based on the tool position, e.g., where the tool passes through the virtual patient's abdomen 308. Tool position can be determined to provide sufficient movement and reach of a tool in the workspace.

Next, in block 144, a position (including location and/or orientation) of one or more virtual surgical robotic arms and/or a surgical robotic platform can be arranged in the virtual surgical operating room based on the tool position, workspace, and/or port position. The surgical robotic arm positions, on which the tools are attached to, can be determined to hold each of the virtual tools in a proper position so that reach and movements in the workspace are sufficient. Height and pitch angles of the platform can be adjusted.

At block 146, the optimization can include arranging a location or orientation of a virtual control tower, a virtual user console, and other surgical robotic equipment. This can be performed based on various factors, for example, minimizing travel of personnel by clustering related tools, placing certain tools and equipment near relevant personnel, providing space for medical personnel and other medical equipment, and minimizing risk of collisions. By using such an order of operations, reach and movement within the workspace, which is critical to the operation, is prioritized. Remaining considerations such as layout of medical equipment for convenience and fit, can be determined without altering the positions of the surgical robotic arms that provide sufficient reach and movement in the workspace.

In one embodiment, a virtual operating room can be generated at block 144. The virtual robotic arm and platform are arranged in the virtual operating room. In this case, the equipment can then be arranged in the virtual operating room in block 146. In another embodiment, the virtual operating room can be generated at block 146 after all the virtual surgical equipment has been positioned. In this manner, assuming that virtual operating rooms are representative of real operating rooms that may be available within a facility, if the availability of operating rooms is high, then the arrangement of the virtual patient and the virtual surgical equipment can be performed first, and then a virtual operating room that represents a physical operating room can be selected to best suit the optimized arrangement, without altering the arrangement. On the other hand, if availability of the operating rooms is low, the operating room can be selected at block 144, and the locations and orientations of the equipment can be arranged and optimized based on restraints inherent to a geometry or size of the available operation room. Thus, the order in which the virtual operating room is determined can shift depending on availability of physical operating rooms.

In one embodiment, based on the optimization process described above, the process can output an optimized room layout 152 (e.g., location and orientation of the surgical robotic arm, platform, user console, control tower, and other surgical equipment) as well as an optimized surgical robotic arm configuration/workflow 154. As described, the optimized workflow can define one or more default trocar/tool positions, port locations, and a position and orientation of each member of the surgical robotic arm.

Figure 5:
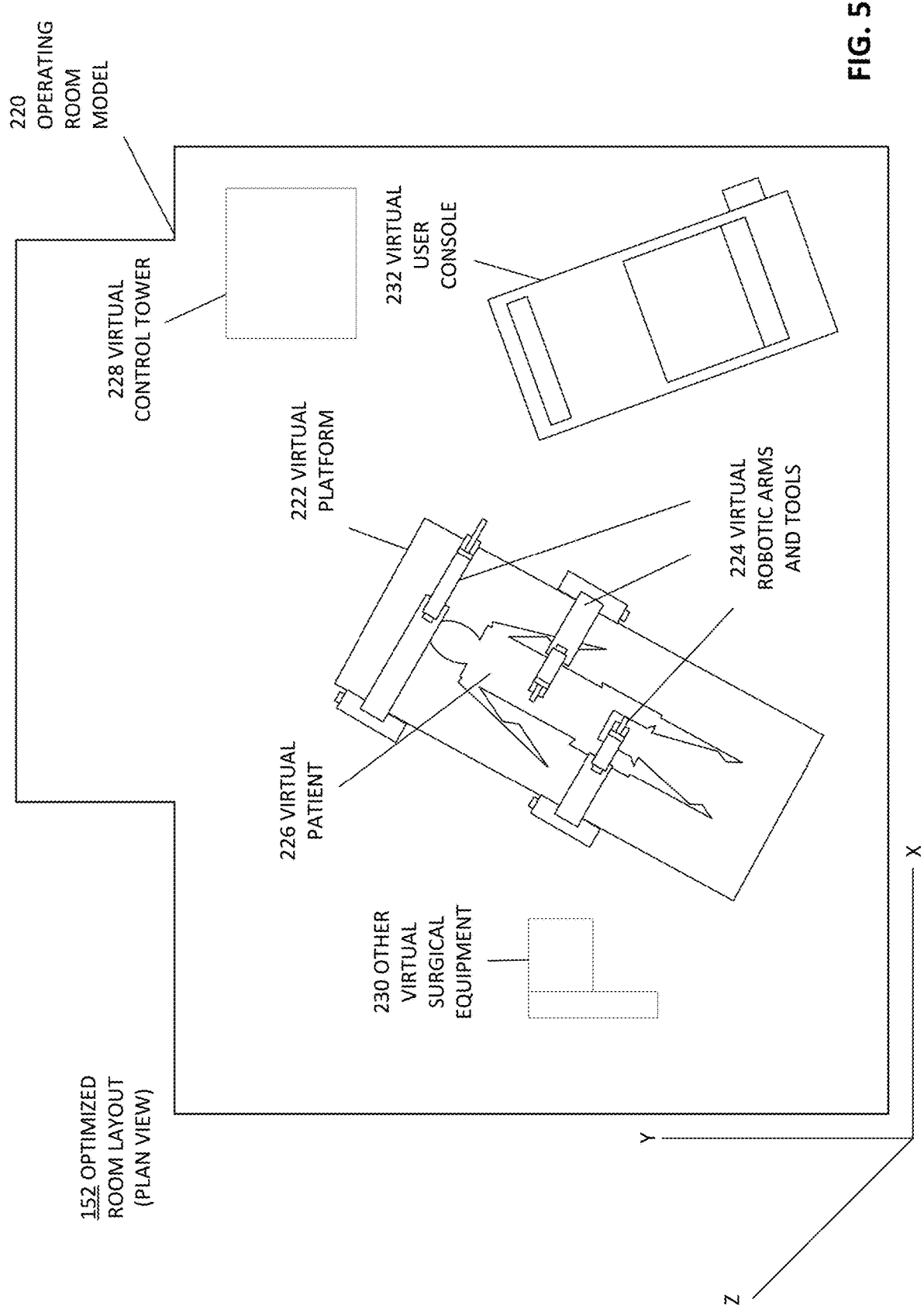
FIG. 5 shows an optimized virtual surgical environment, according to one embodiment.

Referring to FIG. 5, one example is shown of an optimized room layout in plan view. The location of any of the virtual objects, such as but not limited to: virtual patient 226, surgical robotic platform 222, surgical robotic arms and attached tools 224, a virtual control tower 228, a user console 232, and other virtual surgical equipment 230 can be arranged in a virtual surgical environment 220. The arrangement of the virtual objects can be described with coordinates such as, but not limited to, an x, y, and/or z axis. The orientation can describe a direction of any of the objects.

Planning a Virtual Surgical Environment with a Physical Operating Room

Careful planning and visualization can help the setup of a surgical robotic system to support workflow with repeatability and high chance of success. Operating rooms that are not be compatible with surgical robotic systems can be identified with help of a virtual environment.

Figure 6:
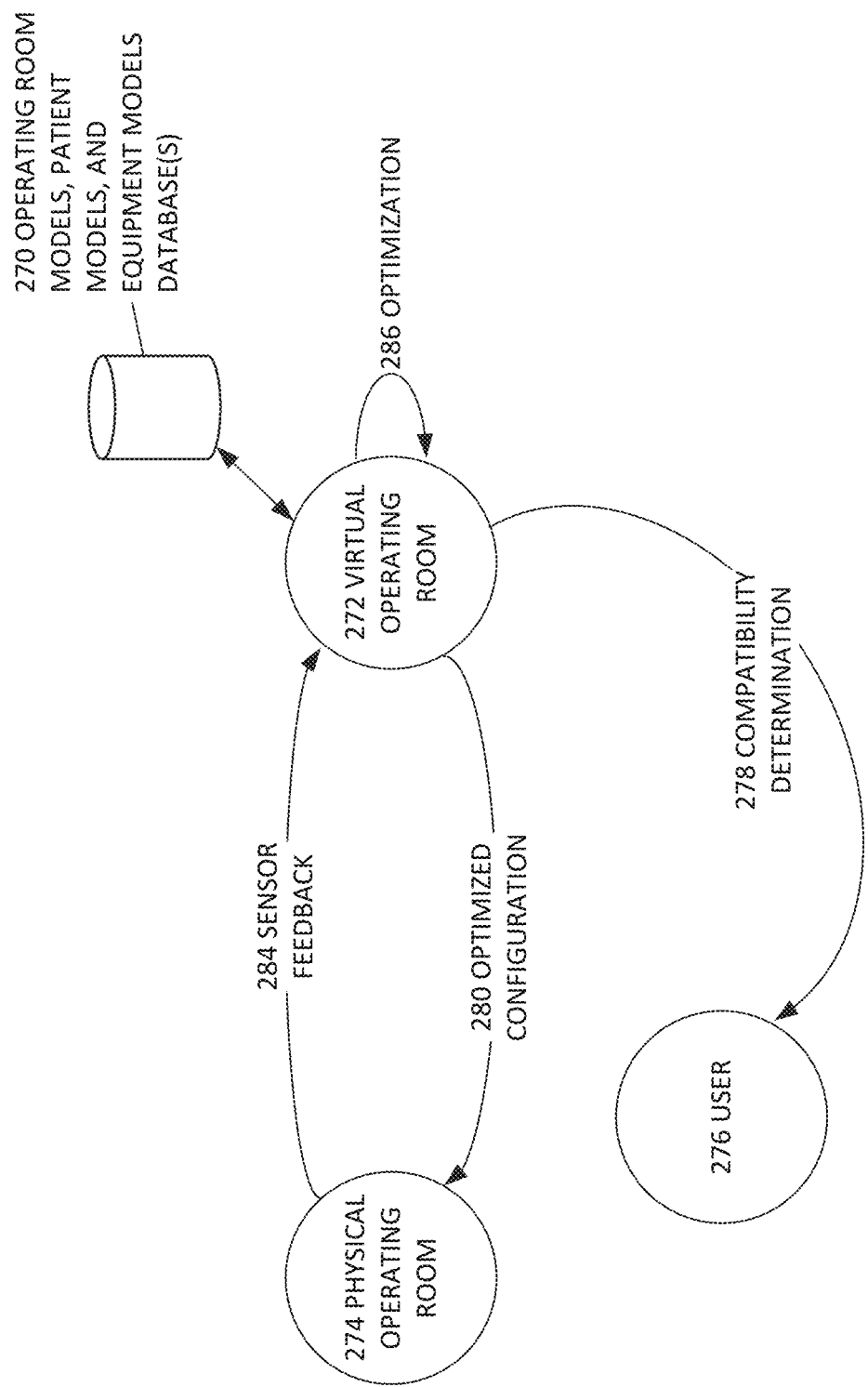
FIG. 6 shows a flow diagram of generating a virtual surgical environment with feedback from a physical OR, according to one embodiment.

In one embodiment, a flow diagram of FIG. 6 shows a method and system that helps determine a layout of surgical equipment based on feedback from a physical operating room. At block 272, a virtual OR is generated that includes virtual surgical equipment. The virtual surgical equipment can include virtual representations of the equipment shown in FIG. 1. The virtual OR and virtual surgical equipment can be generated based on existing operating room models and existing equipment models. These models can be retrieved from one or more databases 270 supported by one or more computing devices either local or networked. The OR models and/or the existing equipment models can include one or more of the following: geometry, size, name, a surgical robotic system configuration, and surgery type. For example, a model of a surgical robotic arm can describe geometry and size of the arm. The model can have a name and have metadata describing what surgery type or types that the arm is suitable for. The surgical robotic system configuration can define one or more of the following: a number of robotic arms, tools (e.g., grasper, stapler, etc.), and pose of the robotic arms. In some embodiments, a virtual patient is generated in the virtual OR, based on a patient model that can be retrieved from the one or more databases.

Sensor feedback can be received at operation 284. The sensor feedback can define geometry of the physical operating room and/or positions of physical surgical equipment in the physical OR. The geometry of the physical operating room shows a shape and size of the room. The positions of the physical equipment can describe a location and orientation of equipment in the room. Sensor feedback can be generated by one or more sensors, including but not limited to: a camera, an infrared sensor, 3D scan cameras, robotic sensors, and human tracking devices. These sensors can be located on walls, in handheld devices, or integrated with surgical robotic equipment.

At block 272, the virtual OR and/or the virtual surgical equipment in the virtual OR is updated based on the sensor feedback. For example, a geometry of the virtual operating room can be updated to match the physical operating room. Similarly, locations and orientations of the virtual surgical equipment can be updated to match the physical surgical equipment in the physical operating room. Object detection and other known computer vision technology can be used to recognize equipment and objects in the sensor feedback. In this manner, the process can automatically detect the physical surgical equipment in the physical operating room and sync the virtual surgical equipment to reflect the positions of the physical surgical equipment.

At operation 286, the layout of the virtual surgical equipment can be optimized. Optimization can include routing cables and fluid lines, for example, to reducing routing in walk zones. Optimization be based on one or more criteria, such as but not limited to: optimized workflow, clearance of the virtual surgical equipment, unobstructed walking paths, close placement of related equipment, reduced length of cables and fluid lines, reduced clutter, and reduced risk of collision. The criteria can be weighted. For example, workflow allows for proper performance of a surgical procedure in a surgical workspace. Therefore, workflow can be assigned a greater weight than convenience based criteria such as convenience reduced clutter. Optimizing can include arranging the virtual surgical equipment in the virtual OR in one or more arrangements and selecting a most favorable of the one or more arrangements based how the criteria are satisfied.

In some embodiments, optimizing the layout of the virtual surgical equipment includes determining an improved geometry of the virtual OR such as changing a shape or size of the virtual OR. The geometry can be changed, for example, based on increasing clearance between equipment or other factors. Optimization can be performed through systems and processes described in relation to the optimization process 110 of FIG. 3 and FIG. 4.

At operation 280, the optimized configuration of the virtual OR and the virtual surgical equipment can be rendered on a display. At block 274, the physical operating room can be adjusted accordingly by personnel. The optimized configuration can be used as a reference for the adjustment.

This process (blocks 274, 284, 272, 286, and 280) can be repeated to form a closed loop that refines the set-up of surgical equipment in the physical operating room. For example, after the physical OR is adjusted, additional sensor feedback is received again at operation 284. The additional sensor feedback can indicate rearrangement of the physical equipment in the physical OR. The virtual operating room and/or layout of the virtual surgical equipment can be updated based on the additional feedback, and the optimization operation can be performed again. An updated optimized configuration can be displayed and used as reference for further rearrangement, and so on. At some point, the optimization operation may not make any changes to the virtual operation room. In such a case, the system and process might not have any additional suggestions regarding the layout of the surgical equipment.

Such a process can be beneficial in planning for surgical robotic procedures using a surgical robotic system (e.g., shown in FIG. 1) because set up of such surgical robotic systems can be challenging due to the various parts (e.g., the surgical robotic arms, platform, user console, control tower, personnel, sensors, and other equipment). As such, not all ORs may be suitable for such a surgical procedure, either due to lack of space or deficiencies in the OR geometry which may cause issues during performance of a surgical procedure.

In some embodiments, sensor position in a physical operating room can be simulated in a virtualized operating room. For example, a surgical robotic system may make use of a camera mounted on a wall. Placement of camera is difficult to plan for because it is difficult to sense occlusions in the line of sight of the camera until after the camera is installed. A virtual camera can be generated in the virtual operating room to help determine a proper location and line of sight of the physical camera.

For example, sensor feedback received at operation 284 can contain camera data (e.g., one or more images) from a physical camera that is in the physical operating room. At block 272, the system can generate and/or update a virtual camera that has a location and line of sight that corresponds to a location and line of sight of the physical camera. At block 286, the system can determine whether occlusion (objects that block vision) is present in the line of sight of the virtual camera. If occlusion is present, the system can modify the location or the line of sight of the virtual camera to minimize or eliminate the occlusion. The virtual camera can be shown in the optimized configuration, which can then be used as a reference to adjust the physical camera.

In one embodiment, the sensory feedback includes control data and sensor data (e.g., encoder data, kinetic data) of a physical surgical robotic arm in the physical OR. Thus, feedback from the physical surgical robotic arm can be used to optimize the virtual OR layout. For example, if the sensor data (e.g., an image) does not include an accurate representation of a physical patient, the processor can use other sensor data (e.g. encoder data from the robotic arm) to parameterize a generalized patient model, and subsequently create a virtual model of the OR layout based on the patient model. Then, the improvement of the OR layout and workflow can be computed as described.

In one embodiment, the system can store the virtual OR with an optimized layout in the one or more databases 270. The stored layout can be called upon and re-used in the future to help adjust a physical operating room, so that the same optimization process is not repeated needlessly.

In one embodiment, based on the sensor feedback (e.g., 3D scans of the physical OR), the system can add new virtual equipment within the virtual OR based on the received data. New models can be generated and stored in the databases. In this manner, the system can add new and unknown virtual objects into the virtual operating room based on feedback from 3D scanners and stitch them into the virtual OR.

The system can generate a report that includes layout information of the equipment models in the virtual OR. The report can include pictures such as plan views of perspective views. The system can determine whether a physical OR has a capacity to support the equipment models or surgical robotic system to be used in a surgical procedure. For example, based on the size and geometry of the room, and the proximity of the equipment to each other, it may be deemed that the physical OR is unsuitable for such equipment and procedure.

In some embodiments, compatibility of an operating room for a surgical robotic procedure and equipment can be determined. A virtual OR can be generated based on geometry of a physical OR. The virtual OR can be generated at block 272 based on pre-existing OR models and equipment models, and/or based on sensed feedback that can be analyzed to determine size and shape of a physical operating room and objects in the physical operating room. At operation 286, the layout of the virtual surgical equipment can be optimized, as described.

At operation 278, a compatibility determination can be performed, describing how compatible a physical OR is for a surgical robotic system and/or procedure. The determination can show how much capacity the OR has to support the virtual surgical robotic system. In one embodiment, the determination can be based on whether the virtual equipment can be reliably moved in and out of the virtual OR, which, in turn, reflects whether the physical equipment can reliably be moved in and out of the physical OR. Compatibility score also be based on comparing the sizes of virtual equipment (e.g., the virtual robotic arm, platform, user console, and control tower), with entrances or pathways of the virtual OR.

Compatibility determination can also be made based on whether a sufficient clearance exists between the virtual surgical equipment, between the virtual surgical equipment and walls of the physical OR, or between the virtual surgical equipment and virtual personnel. Thus, compatibility determinations can also take into account how cramped an OR might be.

At block 276, a user can review the compatibility determination and decide whether to use the current physical operating room for the procedure, or use a different operating room. For example, a low compatibility score may indicate to the user that the current physical operating room is either too small or does not have sufficient entrances to move equipment in and out. In such a case, the user may decide to perform the same process in a different operating room.

In one embodiment, the processor can determine an improved geometry of a hypothetical operating room. This can include determining changes in a shape or size of the current virtual operating room, which can be based on a scan of the physical operating room. The improved geometry can be indicated through a display or report, thereby providing suggestions as to a more suitable OR for the procedure.

In one embodiment, the processor can route virtual cables in the virtual operating room (e.g., between the equipment models and/or between models and electric sockets). Similarly, intravenous lines or other medical tubes or cables can be routed within the virtual operating room. The processor can identify sensitive routes where cabling is laid as 'no-go' zones to aid in the setup and planning of a surgical robotic procedure, and to help train staff.

In one embodiment, the method includes displaying the virtual surgical environment. For example, the virtual surgical environment can be displayed to a user display on the user console (as shown in FIG. 1) or any display, local or remote. The virtual surgical environment can be displayed as a stadium view, plan view, first person view, or other view. The display can be driven by data transfer protocols between nodes (e.g., computing devices) on a network (e.g. TCP/IP, Ethernet, UDP, and more). In one embodiment, the virtual surgical environment is displayed to a head-mounted display. The wearer of the head-mounted display can be tracked such that the wearer can move throughout the virtual surgical environment to gain a three-dimensional understanding of the location and orientation of the various equipment as well as the unoccupied space and walkways within the virtual surgical environment. In one embodiment, the virtual surgical environment is interactive such that the user can adjust the orientation and/or location of objects in the virtual surgical environment (e.g., the virtual surgical robotic arm, the control tower, an angle or height of the surgical robotic platform, an angle of a display, and more).

In one embodiment, the processors of the system (for example, an optimizing processor, a kinematics processor, robot controllers, cameras, displays, and robotic arms) can include a microprocessor and memory. Each processor may include a single processor or multiple processors with a single processor core or multiple processor cores included therein. Each processor may represent one or more general-purpose processors such as a microprocessor, a central processing unit (CPU), or the like. More particularly, each processor may be a complex instruction set computing (CISC) microprocessor, reduced instruction set computing (RISC) microprocessor, very long instruction word (VLIW) microprocessor, or processor implementing other instruction sets, or processors implementing a combination of instruction sets. Each processor may also be one or more special-purpose processors such as an application specific integrated circuit (ASIC), a cellular or baseband processor, a field programmable gate array (FPGA), a digital signal processor (DSP), a network processor, a graphics processor, a communications processor, a cryptographic processor, a co-processor, an embedded processor, or any other type of logic capable of processing instructions.

Modules, components and other features, such as algorithms or method steps described herein can be implemented by microprocessors, discrete hardware components or integrated in the functionality of hardware components such as ASICS, FPGAs, DSPs or similar devices. In addition, such features and components can be implemented as firmware or functional circuitry within hardware devices, however, such details are not germane to embodiments of the present disclosure. It will also be appreciated that network computers, handheld computers, mobile computing devices, servers, and/or other data processing systems which have fewer components or perhaps more components may also be used with embodiments of the disclosure.

Some portions of the preceding detailed descriptions have been presented in terms of algorithms and symbolic representations of operations on data bits within a computer memory. These algorithmic descriptions and representations are the ways used by those skilled in the data processing arts to most effectively convey the substance of their work to others skilled in the art. An algorithm is here, and generally, conceived to be a self-consistent sequence of operations leading to a desired result. The operations are those requiring physical manipulations of physical quantities.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as those set forth in the claims below, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

Embodiments of the disclosure also relate to an apparatus for performing the operations herein. Such a computer program is stored in a non-transitory computer readable medium. A machine-readable medium includes any mechanism for storing information in a form readable by a machine (e.g., a computer). For example, a machine-readable (e.g., computer-readable) medium includes a machine (e.g., a computer) readable storage medium (e.g., read only memory ("ROM"), random access memory ("RAM"), magnetic disk storage media, optical storage media, flash memory devices).

The processes or methods depicted in the preceding figures may be performed by processing logic that comprises hardware (e.g. circuitry, dedicated logic, etc.), software (e.g., embodied on a non-transitory computer readable medium), or a combination of both. Although the processes or methods are described above in terms of some sequential operations, it should be appreciated that some of the operations described may be performed in a different order. Moreover, some operations may be performed in parallel rather than sequentially.

Embodiments of the present disclosure are not described with reference to any particular programming language. It will be appreciated that a variety of programming languages may be used to implement the teachings of embodiments of the disclosure as described herein.

In the foregoing specification, embodiments of the disclosure have been described with reference to specific exemplary embodiments thereof. It will be evident that various modifications may be made thereto without departing from the broader spirit and scope of the disclosure as set forth in the following claims. The specification and drawings are, accordingly, to be regarded in an illustrative sense rather than a restrictive sense. The foregoing description, for purposes of explanation, used specific nomenclature to provide a thorough understanding of the invention. However, it will be apparent to one skilled in the art that specific details are not required in order to practice the invention. Thus, the foregoing descriptions of specific embodiments of the invention are presented for purposes of illustration and description. They are not intended to be exhaustive or to limit the invention to the precise forms disclosed; obviously, many modifications and variations are possible in view of the above teachings. The embodiments were chosen and described in order to best explain the principles of the invention and its practical applications, and they thereby enable others skilled in the art to best utilize the invention and various embodiments with various modifications as are suited to the particular use contemplated. It is intended that the following claims and their equivalents define the scope of the invention.

What is claimed is:

1. A method performed by one or more processors, comprising:
  processing one or more images from a camera to determine a layout of a physical surgical equipment within a physical operating room (OR);
  generating a virtual surgical equipment within a virtual OR with a layout that is matched to the layout of the physical surgical equipment within the physical OR;
  determining a compatibility determination for the layout of the virtual surgical equipment within the virtual OR, wherein the compatibility determination indicates whether the virtual surgical equipment may be reliably moved in and out of the virtual OR;

responsive to the compatibility determination indicating that the virtual surgical equipment cannot be reliably moved in and out of the virtual OR, changing a geometry of the virtual OR to allow the virtual surgical equipment to be reliably moved in and out of the virtual OR; and presenting the virtual OR to a head-mounted display (HMD) as a three-dimensional (3D) virtual reality (VR) simulation.

2. The method of claim 1, wherein the compatibility determination is determined based on a clearance between the virtual surgical equipment in the virtual OR.

3. The method of claim 1, wherein the compatibility determination is determined based on a clearance between the virtual surgical equipment and a virtual person in the virtual OR.

4. The method of claim 1, wherein the compatibility determination is determined based on comparing a size of the virtual surgical equipment with an entrance of the virtual OR.

5. The method of claim 1, wherein the compatibility determination is determined based on comparing a size of the virtual surgical equipment with a pathway of the virtual OR.

6. The method of claim 1, further comprising adjusting a location or an orientation of the virtual surgical equipment in response to input from a user from within the 3D VR simulation.

7. The method of claim 6, wherein moving the virtual surgical equipment in response to the input from the user includes adjusting an angle or height of a surgical platform.

8. The method of claim 6, wherein moving the virtual surgical equipment in response to the input from the user includes adjusting a location or orientation of a robotic arm.

9. The method of claim 1, wherein processing the one or more images from the camera to determine the layout of the physical surgical equipment within the physical OR includes using computer vision to detect the physical surgical equipment and its position in the physical OR.

10. A system, comprising:

a head mounted display (HMD) worn by a user to move through a three-dimensional (3D) virtual reality (VR) simulation; and a processor, configured to:

process one or more images from a camera to determine a layout of a physical surgical equipment within a physical operating room (OR);

generate a virtual surgical equipment within a virtual OR with a layout that is matched to the layout of the physical surgical equipment within the physical OR;

determine a compatibility determination for the layout of the virtual surgical equipment within the virtual OR, wherein the compatibility determination indicates whether the virtual surgical equipment may be reliably moved in and out of the virtual OR;

responsive to the compatibility determination indicating that the virtual surgical equipment cannot be reliably moved in and out of the virtual OR, changing a geometry of the virtual OR to allow the virtual surgical equipment to be reliably moved in and out of the virtual OR; and present the virtual OR in the VR simulation to the HMD.

11. The system of claim 10, wherein the compatibility determination is determined based on a clearance between the virtual surgical equipment in the virtual OR.

12. The system of claim 10, wherein the compatibility determination is determined based on a clearance between the virtual surgical equipment and a virtual person in the virtual OR.

13. The system of claim 10, wherein the compatibility determination is determined based on comparing a size of the virtual surgical equipment with an entrance of the virtual OR.

14. The system of claim 10, wherein the compatibility determination is determined based on comparing a size of the virtual surgical equipment with a pathway of the virtual OR.

15. The system of claim 10, wherein the processor is further to adjust a location or an orientation of the virtual surgical equipment in response to input from the user from within the 3D VR simulation.

16. The system of claim 15, wherein moving the virtual surgical equipment in response to the input from the user includes adjusting an angle or height of a surgical platform.

17. The system of claim 15, wherein moving the virtual surgical equipment in response to the input from the user includes adjusting a location or orientation of a robotic arm.

18. The system of claim 10, wherein processing the one or more images from the camera to determine the layout of the physical surgical equipment within the physical OR includes using computer vision to detect the physical surgical equipment and its position in the physical OR.

* * * * *